US011957675B2

(12) United States Patent
Pimstone (10) Patent No.: US 11,957,675 B2
(45) Date of Patent: Apr. 16, 2024

(54) METHODS AND USES FOR TREATING ANHEDONIA

(71) Applicant: XENON PHARMACEUTICALS INC., Burnaby (CA)

(72) Inventor: Simon Neil Pimstone, Vancouver (CA)

(73) Assignee: Xenon Pharmaceuticals Inc., Burnaby (CA)

( * ) Notice: Subject to any disclaimer, the term of this patent is extended or adjusted under 35 U.S.C. 154(b) by 0 days.

(21) Appl. No.: 17/668,340

(22) Filed: Feb. 9, 2022

(65) Prior Publication Data

US 2022/0265634 A1 Aug. 25, 2022

Related U.S. Application Data

(60) Provisional application No. 63/147,742, filed on Feb. 9, 2021.

(51) Int. Cl.
*A61K 31/472* (2006.01)
*A61P 25/24* (2006.01)

(52) U.S. Cl.
CPC ............ *A61K 31/472* (2013.01); *A61P 25/24* (2018.01)

(58) Field of Classification Search
CPC .............................. A61K 31/472; A61P 25/24
See application file for complete search history.

(56) References Cited

U.S. PATENT DOCUMENTS

| | | | |
|---|---|---|---|
| 8,293,911 B2 * | 10/2012 | Vernier | A61P 25/08 546/144 |
| 8,993,593 B2 | 3/2015 | Vernier et al. | |
| 11,091,441 B2 | 8/2021 | Bichler et al. | |
| 11,135,214 B2 | 10/2021 | Beatch | |
| 2008/0139610 A1 | 6/2008 | Vernier et al. | |
| 2009/0318507 A2 | 12/2009 | Rundfeldt et al. | |
| 2010/0256145 A1 * | 10/2010 | Bak-Jensen | A61P 15/10 514/235.5 |
| 2011/0003850 A1 | 1/2011 | Vernier et al. | |
| 2019/0343823 A1 | 11/2019 | Beatch | |
| 2021/0161886 A1 | 6/2021 | Harden et al. | |
| 2022/0062266 A1 * | 3/2022 | Beatch | A61K 9/0053 |
| 2023/0015539 A1 | 1/2023 | Murrough et al. | |

FOREIGN PATENT DOCUMENTS

| | | |
|---|---|---|
| WO | WO 2008/024398 A2 | 2/2008 |
| WO | WO 2019/217924 A1 | 11/2019 |
| WO | WO 2021/092439 A1 | 5/2021 |
| WO | WO 2021/113802 A1 | 6/2021 |

OTHER PUBLICATIONS

International Search Report and Written Opinion, mailed May 11, 2022 for International Application No. PCT/US2022/015854.
International Preliminary Report on Patentability, mailed Aug. 24, 2023 for International Application No. PCT/US2022/015854.
[No Author Listed], Xenon Pharmaceuticals Announces Promising New Pre-Clinical Data and Provides Clinical Overview of its XEN1101 Program at ASENT 2021. Xenon Pharmaceuticals Inc. (Feb. 22, 2021) Accessed from <https://investor.xenon-pharma.com/news-releases/news-release-details/xenon-pharmaceuticals-announces-promising-new-pre-clinical-data>. 4 pages.
Can et al., The mouse forced swim test. J Vis Exp. (Jan. 29, 2012) 59:e3638. 5 pages. doi: 10.3791/3638.
Costi et al., Impact of the KCNQ2/3 Channel Opener Ezogabine on Reward Circuit Activity and Clinical Symptoms in Depression: Results From a Randomized Controlled Trial. Am J Psychiatry. (May 1, 2021) 178(5):437-446. doi: 10.1176/appi.ajp.2020.20050653.
Cutts, A., Depression and Anhedonia: Acute Preclinical Efficacy for XEN1101, a Differentiated Kv7 Potassium Channel Modulator. Xenon Pharmaceuticals Inc. Virtual Meeting of the American Society of Experimental Neurotherapeutics. Feb. 24, 2021. Presentation. 8 pages.
Cutts, A., Abstract for Depression and Anhedonia: Acute Preclinical Efficacy for XEN1101, a Differentiated Kv7 Potassium Channel Modulator. Xenon Pharmaceuticals Inc. Accessed from <https://asent2021.b2b-wizard.com/expo/posters/5351>. Feb. 24, 2021. 8 pages.
Cutts et al., XEN1101, a Differentiated Kv7 Potassium Channel Modulator, Impacts Depression and Anhedonia. Xenon Pharmaceuticals Inc. 2021 Annual Meeting of the American Epilepsy Society (AES). Dec. 5, 2021. Poster.
Cutts et al., Abstract for XEN1101, a Differentiated Kv7 Potassium Channel Modulator, Impacts Depression and Anhedonia. Xenon Pharmaceuticals Inc. Accessed from <https://cms.aesnet.org/abstractslisting/xen1101—a-differentiated-kv7-potassium-channel-modulator--impacts-depression-and-anhedonia>. Nov. 22, 2021. 2 pages.
Enna et al., The GABA Receptors. In: Enna and Möhler, The GABA Receptors, Third Edition. (2007) Humana Press Inc, Totowa, NJ. 26 pages.
Friedman et al., KCNQ channel openers reverse depressive symptoms via an active resilience mechanism. Nat Commun. (May 24, 2016) 24;7:11671. 7 pages. doi: 10.1038/ncomms11671.
Greenfield, L.J., Molecular mechanisms of antiseizure drug activity at $GABA_A$ receptors. Seizure. (2013) 22(8):589-600. doi: 10.1016/j.seizure.2013.04.015.
Luscher et al., The GABAergic deficit hypothesis of major depressive disorder. Mol Psychiatry. (2011) 16(4):383-406. doi: 10.1038/mp.2010.120. Author Manuscript, 41 pages.
Sherrington, R., Kv7 Modulators in Epilepsy and Depression. Xenon Pharmaceuticals Inc. Virtual Meeting of the American Society of Experimental Neurotherapeutics. Feb. 24, 2021. Presentation. 16 pages.

(Continued)

*Primary Examiner* — Timothy R Rozof (74) *Attorney, Agent, or Firm* — Wolf, Greenfield & Sacks, P.C.

(57) ABSTRACT

The present disclosure is directed to, among other things, methods and uses for treating anhedonia in a subject, such as a human, wherein the methods comprise administering a therapeutically effective amount of N-[4-(6-fluoro-3,4-dihydro-1H-isoquinolin-2-yl)-2,6-dimethylphenyl]-3,3-dimethylbutanamide (Compound A) to the subject in need thereof, and the uses comprise Compound A for use in treating anhedonia in a subject, such as a human. The present disclosure is further directed to various improved methods of therapy and administration of Compound A.

36 Claims, 3 Drawing Sheets

(56) References Cited

OTHER PUBLICATIONS

Tan et al., Effects of the KCNQ channel opener ezogabine on functional connectivity of the ventral striatum and clinical symptoms in patients with major depressive disorder. Mol Psychiatry. (Nov. 1, 2018) 25(6):1323-1333. doi: 10.1038/s41380-018-0283-2.
Treven et al., The anticonvulsant retigabine is a subtype selective modulator of $GABA_A$ receptors. Epilepsia. (2015) 56(4):647-657. doi: 10.1111/epi.12950.

* cited by examiner

METHODS AND USES FOR TREATING ANHEDONIA

1. BACKGROUND

Anhedonia is characterized by a reduced ability to experience pleasure and/or a diminished interest in engaging in pleasurable activities and is a prominent symptom of many neuropsychiatric disorders. The severity of anhedonia may be quantified according to the 14-point Snaith-Hamilton Pleasure Scale (SHAPS). Snaith et al., Br. J. Psychiatry 1995; 167: 99-103; Nakonezny et al., Int. Clin. Psychopharmacol. 2010; 25(6): 328-333.

Anhedonia frequently occurs in depression, e.g. in major depressive disorder and stress-induced depression. Anhedonia is a core symptom of major depressive disorder and is found in roughly 70% of people suffering from this condition. Individuals experiencing anhedonia can be diagnosed with depression, even in the absence of other symptoms reflective of a low or depressed mood.

Anhedonia is commonly listed as one component of negative symptoms in schizophrenia. Although five domains are usually used to classify negative schizophrenia symptoms, factor analysis of questionnaires yield two factors, with one including deficits in pleasure and motivation. People with schizophrenia retrospectively report experiencing fewer positive emotions than healthy individuals.

Anhedonia is associated with substance use disorders and negatively impacts treatment outcomes. Anhedonia is common in people who are dependent on a wide variety of drugs, including alcohol, opioids, and nicotine.

Anhedonia occurs frequently in Parkinson's disease, with rates between 7%-45% being reported. Anhedonia also occurs in obsessive-compulsive disorders (such as overeating syndrome).

Social anhedonia is defined as a disinterest in social contact and a lack of pleasure in social situations, and is characterized by social withdrawal. This characteristic typically manifests as an indifference to social interactions with other people.

Sexual anhedonia is most frequently found in males, and is sometimes referred to as "ejaculatory anhedonia." Men suffering from this condition will ejaculate with no accompanying sense of pleasure. Sexual anhedonia also occurs in women and manifests as lack of pleasure accompanying orgasm. Use of selective serotonin reuptake inhibitors (SSRIs) can cause sexual anhedonia.

Depression is a leading cause of disability worldwide. Available treatments, however, are only partially effective for many patients and are associated with additional limitations, including a slow onset of therapeutic action and undesirable side effects. Currently, the U.S. Food and Drug Administration (FDA)-approved treatments for depression mostly consist of serotonergic and noradrenergic agents, which largely share the same basic pharmacology and mechanism of action based on decades-old discoveries. This lack of mechanistic diversity leaves little opportunity for improved patient outcomes or personalized treatment approaches.

Given the occurrence of anhedonia, including in the various diseases and conditions described above, there is a need for corresponding anhedonia treatments.

2. SUMMARY

The present disclosure describes certain methods and uses for the small molecule N-[4-(6-Fluoro-3,4-dihydro-1H-isoquinolin-2-yl)-2,6-dimethylphenyl]-3,3-dimethylbutanamide (herein referred to as "Compound A").

In one embodiment, the present disclosure is directed to a method of treating anhedonia in a subject in need thereof (preferably, a mammal, such as a human), comprising administering (e.g., orally) a therapeutically effective amount of Compound A to the subject. In some embodiments, the present disclosure is directed to the use of Compound A in treating anhedonia in a subject in need thereof (preferably, a mammal, such as a human). In some embodiments, the anhedonic subject suffers from sexual anhedonia or social anhedonia. In some instances, the aforesaid method or use comprises reversing hyperactivity in the ventral tegmental area (VTA) in the subject having anhedonia.

In one embodiment the anhedonia, prior to treatment with Compound A, has a severity of at least 4 as measured by SHAPS. In other embodiments the anhedonia, prior to treatment with Compound A, has a severity of at least 5, at least 6, at least 7, at least 8, at least 9, at least 10, at least 11, at least 12, at least 13, or 14 as measured by SHAPS.

In certain instances, the anhedonia treated by the administration of Compound A is a symptom of a neuropsychiatric disorder such as a depressive disorder, substance-related disorder, psychotic disorder, personality disorder, epileptic disorder, or a combination thereof. In one embodiment, the depressive disorder is major depressive disorder (MDD). In some embodiments the depressive disorder is post-traumatic stress disorder (PTSD), disruptive mood dysregulation disorder, persistent depressive disorder, bipolar spectrum disorder, bipolar depression, postpartum depression, premenstrual dysphoric disorder (PMDD), seasonal affective disorder (SAD), atypical depression, treatment-resistant depression (TRD), depression associated with agitation or anxiety, adjustment disorder with depressed mood, prolonged depressive reaction, or a combination thereof. In some embodiments, the substance-related disorder comprises a dependency on one or more drugs, including alcohol, cocaine, opioids, nicotine, or a combination thereof. In some embodiments, the neuropsychiatric disorder is schizophrenia, schizoaffective disorder, or schizotypal disorder. In some embodiments, the neuropsychiatric disorder is an obsessive-compulsive disorder, such as overeating syndrome. In some embodiments, the neuropsychiatric disorder is extrapyramidal disorder, Alzheimer's disease, dementia, Parkinson's disease, PTSD, anorexia nervosa, panic disorder, attention deficit hyperactivity disorder (ADHD), chronic headache including chronic migraine with or without aura, migraine aura without headache, chronic tension headache, hemicrania continua, new daily persistent headache, dementia, multiple sclerosis or dysthymic disorder. In some embodiments, the epileptic disorder is epilepsy focal onset epilepsy or post stroke epilepsy. In some embodiments, the anhedonia treated by the administration of Compound A is associated with, cancer, chronic pain, HIV/AIDs, lupus, or hypothyroidism.

In an additional embodiment, the method of treating anhedonia comprising administering a therapeutically effective amount of Compound A, or the use of Compound A in treating anhedonia, further comprises enhancing the opening of a Kv7 potassium channel in the subject (e.g., human).

In another embodiment, the present disclosure is directed to a method of opening or enhancing the opening of a Kv7 potassium channel in a subject (preferably, a mammal, such as a human), comprising administering an effective amount of Compound A to the subject, or the use of Compound A in opening or enhancing the opening of a Kv7 potassium channel in a subject, wherein the subject is suffering from anhedonia such as the various types of anhedonia and disorders having symptoms of anhedonia described herein, including anhedonia associated with major depressive disorder (MDD), post-traumatic stress disorder (PTSD), schizophrenia, substance-related disorders, Parkinson's disease, depression associated with agitation or anxiety, epilepsy, or obsessive-compulsive disorder (e.g. overeating syndrome).

In some aspects, the Kv7 potassium channel is one or more of Kv7.2, Kv7.3, Kv7.4, or Kv7.5. In certain instances, the opening or enhanced opening of one or more of the Kv7.2, Kv7.3, Kv7.4, or Kv7.5 potassium channels is selective over Kv7.1. In other instances, the method comprises opening or enhanced opening of the Kv7.2/Kv7.3 (KCNQ2/3) potassium channel.

In certain instances, the administration of Compound A to the subject comprises administering a dose of 2 to 200 mg of Compound A per administration. In other instances, the administration to the subject comprises a dose of 5-1000 mg given daily, on alternate days, or weekly. In further instances, the administration to the subject comprises a dose of 0.05-20 mg/kg, such as 0.1-5 mg/kg given daily, on alternate days, or weekly.

In some embodiments of the present methods and uses, Compound A is orally administered to the subject (preferably, a mammal, such as a human) from between about 30 minutes before to about 2 hours after eating a meal, for example, Compound A may be orally administered to the subject during a meal or within 15 minutes after eating a meal. Alternatively, Compound A may be orally administered to the subject without regard to the timing of a previous or subsequent meal.

Compound A is a small molecule currently being developed for the treatment of seizure disorders, and its use as a potassium channel modulator is disclosed in U.S. Pat. Nos. 8,293,911 and 8,993,593 as well as U.S. application Ser. Nos. 16/409,684 and 16/410,851, the disclosures of which are hereby incorporated by reference in their entireties.

These and other aspects of this disclosure will be apparent upon reference to the following detailed description. To this end, various references are set forth herein which describe in more detail certain background information and procedures and are each hereby incorporated by reference in their entirety.

4. DETAILED DESCRIPTION

The present disclosure relates to novel and improved methods and uses for Compound A, particularly for treatment of anhedonia by administering Compound A to a subject in need thereof (preferably, a mammal, such as a human) by oral administration or by other routes.

In the following disclosure, certain specific details are set forth in order to provide a thorough understanding of various embodiments. However, one skilled in the art will understand that the methods and uses described herein may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

4.1. Definitions

As used in the specification and appended claims, unless specified to the contrary, the following terms and abbreviations have the meaning indicated:

"Anhedonia" as used herein refers to markedly diminished interest or pleasure in all, or almost all activities. Anhedonia of mild degree is sometimes referred to as hypohedonia.

"Compound A" refers to the compound having the following formula:

and having a chemical name of N-[4-(6-fluoro-3,4-dihydro-1H-isoquinolin-2-yl)-2,6-dimethylphenyl]-3,3-dimethylbutanamide. Preparation of Compound A and its use as a Kv7.2/Kv7.3 (KCNQ2/3) opener is disclosed in U.S. Pat. Nos. 8,293,911 and 8,993,593 as well as U.S. application Ser. Nos. 16/409,684 and 16/410,851. Compound A potentiates and enhances opening of the voltage-gated potassium channels Kv7.2 and Kv7.3 (Kv7.2/Kv7.3), which are important in controlling neuronal excitability. Compound A is used in the methods and uses described herein.

"Social anhedonia" as used herein refers to a disinterest in social contact and a lack of pleasure in social situations. Social anhedonia is characterized by social withdrawal and typically manifests as an indifference to social interactions with other people. This trait is considered to be a central characteristic, as well as a predictor, of schizophrenia spectrum disorders.

"Therapeutically effective amount" as used herein refers to an amount of Compound A that is sufficient to treat the stated disease, disorder, or condition or have the desired stated effect on the disease, disorder, or condition or one or more mechanisms underlying the disease, disorder, or condition in a human subject. In certain embodiments, when Compound A is administered for the treatment of anhedonia, therapeutically effective amount refers an amount of Compound A that, upon administration to a human, treats or ameliorates anhedonia in the human, or exhibits a detectable therapeutic effect in the human having anhedonia. The effect can be detected by, for example, a reduction in the number of anhedonia symptoms (e.g., "liking" or "wanting") or by the reduction of the severity of anhedonia.

"Treatment" as used herein refers to therapeutic applications associated with administering Compound A that ameliorate the indicated disease, disorder, or condition or one or more underlying mechanisms of said disease, disorder, or condition, including slowing or stopping progression of the disease, disorder or condition or one or more of the underlying mechanisms in a human subject. In certain embodiments, when Compound A is administered for the treatment of anhedonia, treatment refers to therapeutic applications to slow or stop progression of anhedonia (i.e., slow or stop the increase in intensity or frequency of anhedonia) and/or reversal of anhedonia. Reversal of anhedonia differs from a therapeutic application which slows or stops anhedonia in that with a method of reversing, not only is progression of anhedonia stopped, but cellular behavior is moved to some degree toward a normal state that would be observed in the absence of the anhedonia. In some embodiments, the treatment of anhedonia comprising the administration of Compound A is accompanied by an alteration of the cellular activity of one or more Kv7 potassium channels (e.g., Kv7.2, Kv7.3, Kv7.4, and/or Kv7.5, particularly Kv7.2 and/or Kv7.3, optionally over Kv7.1) toward a normal level that would be observed in the absence of the anhedonia.

"Under fed conditions" refers to the condition of having consumed food during the time period between from about 4 hours prior to the oral administration of Compound A to about 4 hours after the administration of Compound A. The food may be a solid, liquid, or mixture of solid and liquid food with sufficient bulk and fat content that it is not rapidly dissolved and absorbed in the stomach. In some instances, the food is a meal, such as breakfast, lunch, dinner or, alternatively, baby food (e.g., formula or breast milk). Compound A may be orally administered to the subject, for example, between about 30 minutes before to about 2 hours after eating a meal, most advantageously, Compound A is orally administered during a meal or within 15 minutes after eating a meal.

"Under fasted conditions" refers to the condition of not having consumed food during the time period between from at least 4 hours prior to the oral administration of Compound A to about 4 hours after administration of Compound A.

4.2. Embodiments

Provided herein are methods and uses of the Kv7 activator known as Compound A (N-[4-(6-fluoro-3,4-dihydro-1H-isoquinolin-2-yl)-2,6-dimethylphenyl]-3,3-dimethylbutanamide) as a treatment of anhedonia. In certain instances, the methods and uses operate by reversing hyperactivity in the ventral tegmental area (VTA), e.g., through enhancement of the Kv7 mediated M-current. The anhedonia includes those listed for the disorders disclosed herein, e.g., anhedonia associated with depression (e.g. major depressive disorder) as well as social anhedonia.

This disclosure describes studies of established models of stress-induced depression and anhedonia. For example, CSDS-vulnerable animals can be studied for social avoidance (resident/intruder paradigm) and in the forced swim test for antidepressant activity of Compound A. Such vulnerable animals can also be studied for sucrose preference for effects on treating anhedonia.

In clinical studies, anhedonia assessments in humans can be made using Snaith-Hamilton Pleasure Scale (SHAPS), Temporal Experience of Pleasure Scale (TEPS), Effort Expenditure for Rewards Task (EEfTR), Fawcett-Clark Pleasure Capacity Scale-Physical Pleasure (FCPCS), or Physical Anhedonia Scale of Chapman (PAS), for example to compare the effect of Compound A to placebo.

In some embodiments, the present disclosure is directed to a method of treating anhedonia in a subject in need thereof (preferably, a mammal, such as a human), comprising administering (e.g., orally) a therapeutically effective amount of Compound A to the subject. Similarly, in certain embodiments, the present disclosure is directed to the use of Compound A in treating anhedonia in a subject in need thereof (preferably, a mammal, such as a human).

In some instances, the anhedonic subject treated by the administration of Compound A suffers from sexual anhedonia or social anhedonia. In other instances, the anhedonic subject treated by the administration of Compound A does not suffer from sexual anhedonia or social anhedonia. In certain instances, the anhedonia treated by the administration of Compound A is a symptom of a neuropsychiatric disorder such as a depressive disorder, substance-related disorder, psychotic disorder, personality disorder, epileptic disorder, or a combination thereof.

In certain embodiments, the neuropsychiatric disorder is a depressive disorder. In some such embodiments, the depressive disorder is stress-induced depression, major depressive disorder (MDD), post-traumatic stress disorder (PTSD), disruptive mood dysregulation disorder, persistent depressive disorder, bipolar spectrum disorder, bipolar depression, postpartum depression, premenstrual dysphoric disorder (PMDD), seasonal affective disorder (SAD), atypical depression, treatment-resistant depression (TRD), depression associated with agitation or anxiety, adjustment disorder with depressed mood, prolonged depressive reaction, or a combination thereof. In a particular embodiment, the depressive disorder is MDD.

In other embodiments, the neuropsychiatric disorder is a substance-related disorder. In some embodiments, the substance-related disorder comprises a dependency on one or more drugs, including alcohol, cocaine, opioids, nicotine, or a combination thereof.

In some embodiments, the neuropsychiatric disorder is schizophrenia, schizoaffective disorder, schizotypal disorder, extrapyramidal disorder, Alzheimer's disease, dementia, Parkinson's disease obsessive-compulsive disorder, PTSD, anorexia nervosa, panic disorder, attention deficit hyperactivity disorder (ADHD), chronic headache including chronic migraine with or without aura, migraine aura without headache, chronic tension headache, hemicrania continua, new daily persistent headache, dementia, multiple sclerosis or dysthymic disorder.

In some embodiments, the epileptic disorder is epilepsy, focal onset epilepsy or post stroke epilepsy.

In some embodiments, the anhedonia treated by the administration of Compound A is associated with cancer, chronic pain, HIV/AIDs, lupus, or hypothyroidism.

In some embodiments, the method of treating anhedonia by administering a therapeutically effective amount of Compound A, or the use of Compound A in treating anhedonia, comprises enhancing the opening of a Kv7 potassium channel in the subject (preferably, a mammal, such as a human).

In certain instances, the methods and uses described herein comprise selectively opening or enhancing the opening of a Kv7 potassium channel, such as one or more of Kv7.2, Kv7.3, Kv7.4, or Kv7.5 over Kv7.1. In some embodiments, the method or use is selective for Kv7.2, over Kv7.1. In other embodiments, the method or use is selective for Kv7.3, over Kv7.1. In yet other embodiments, the method or use is selective for Kv7.4, over Kv7.1. In yet further other embodiments, the method or use is selective for Kv7.5, over Kv7.1. In certain embodiments, the method or use is selective for Kv7.2 and Kv7.3, over Kv7.1. In certain embodiments, the method or use is selective for Kv7.2 and Kv7.3 over other Kv7 potassium channels. In certain embodiments, the method or use is selective for Kv7.2 and Kv7.3 over Kv7.4 and Kv7.5.

In certain embodiments, the present disclosure provides methods for reversing hyperactivity in the ventral tegmental area (VTA) in a subject in need thereof (preferably, a mammal, such as a human, for example who is suffering from anhedonia), comprising administering (e.g., orally) an effective amount of Compound A to the subject. Similarly, in some embodiments, the present disclosure is directed to the use of Compound A in reversing hyperactivity in the VTA in a subject in need thereof (preferably, a mammal, such as a human, for example who is suffering from anhedonia).

In certain instances, the method or use described herein comprises selectively opening or enhancing the opening of a Kv7 potassium channel, such as one or more of Kv7.2, Kv7.3, Kv7.4, or Kv7.5 over Kv7.1. In some embodiments, the method or use is selective for Kv7.2, over Kv7.1. In other embodiments, the method or use is selective for Kv7.3, over Kv7.1. In yet other embodiments, the method or use is selective for Kv7.4, over Kv7.1. In yet further other embodiments, the method or use is selective for Kv7.5, over Kv7.1. In certain embodiments, the method or use is selective for Kv7.2 and Kv7.3, over Kv7.1. In certain embodiments, the method or use is selective for Kv7.2 and Kv7.3 over other Kv7 potassium channels. In certain embodiments, the method or use is selective for Kv7.2 and Kv7.3 over Kv7.4 and Kv7.5.

In some embodiments, the treatment of anhedonia is achieved through administration of Compound A to the patient. Such administration may be, e.g., by oral, inhaled, sublingual, buccal, ocular, otic, vaginal, rectal, cutaneous, topical, or transdermal administration; by intravenous, intramuscular, intrathecal, or subcutaneous injection; or by implantation. In certain embodiments, the administration is oral administration.

As an alternative to oral administration, in certain instances other routes of administration of Compound A can be employed in the methods and uses described herein, such as parenteral administration. Parenteral administration routes include subcutaneous, intravenous, intramuscular, intra-articular, intra-synovial, intrasternal, intrathecal, intrahepatic, intralesional, and intracranial injection or infusion techniques or by implantation or inhalation. For example, Compound A can be administered by injection, such as by intravenous, intramuscular, intrathecal, or subcutaneous injection. In certain embodiments, the doses of Compound A discussed herein are intended for oral administration and can be converted to doses suitable for parenteral administration, including administration by injection, by reducing the oral dose, for example by about half.

Other administration routes suitable for administration of Compound A according to the methods and uses described herein include sublingual and buccal (e.g., with a film or other composition that dissolves in the mouth under the tongue or on the inside of the cheek), occular (e.g., eye drops), otic (e.g., by ear drops), oral or nasal inhalation (e.g., by insufflation or nebulization), cutaneous or topical (e.g., by creams or lotions), or transdermal (e.g., by skin patches). Besides oral administration, other enteral administration routes can be used for Compound A, including vaginal and rectal (e.g., by ointment, suppository, enema).

In one embodiment, the methods and uses described herein, such as the method of or use in treating anhedonia in a subject in need thereof (preferably, a mammal, such as a human), is achieved by administering (e.g., orally) a therapeutically effective amount of Compound A, such as from about 0.05 mg/kg to about 20 mg/kg, including from about 0.05 mg/kg to about 10 mg/kg, from about 0.1 mg/kg to about 20 mg/kg, from about 0.1 mg/kg to about 10 mg/kg, from about 0.05 mg/kg to about 5 mg/kg, from about 0.1 mg/kg to about 5 mg/kg, from about 0.05 mg/kg to about 2 mg/kg, or from about 0.1 mg/kg to about 2 mg/kg. More specific representative amounts include 0.05 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 5 mg/kg, 8 mg/kg, 10 mg/kg, 12 mg/kg, 15 mg/kg, 18 mg/kg, or 20 mg/kg or any range of amounts created by using two of the aforementioned amounts as endpoints. In some aspects, the method or use includes administering (e.g., orally) 0.1-5 mg/kg of Compound A. In certain aspects, the method includes administering (e.g., orally) 0.2-0.5 mg/kg of Compound A. In some aspects, the method or use includes administering (e.g., orally) 0.05-20 mg/kg of Compound A. In certain aspects, the method includes administering (e.g., orally) 1-10 mg/kg of Compound A.

In certain instances, the present disclosure provides a method of treating anhedonia in a subject in need thereof (preferably, a mammal, such as a human) comprising administering (e.g., orally) a therapeutically effective amount of Compound A to the subject, wherein the anhedonia includes the various types of anhedonia and disorders having symptoms of anhedonia described herein, including stress-induced depression, major depressive disorder (MDD), post-traumatic stress disorder (PTSD), schizophrenia, substance-related disorders, Parkinson's disease, epilepsy, sexual anhedonia, and social anhedonia, and wherein Compound A is administered at a dose of 0.05-5 mg/kg to the subject, such as 0.1-5 mg/kg, 0.05-2 mg/kg, or 0.1-2 mg/kg, including about 0.05 mg/kg, 0.1 mg/kg, 0.15 mg/kg, 0.2 mg/kg, 0.24 mg/kg, 0.25 mg/kg, 0.3 mg/kg, 0.35 mg/kg, 0.4 mg/kg, 0.5 mg/kg, 0.6 mg/kg, 0.7 mg/kg, 0.75 mg/kg, 0.8 mg/kg, 0.81 mg/kg, 0.85 mg/kg, 0.9 mg/kg, 1 mg/kg, 1.2 mg/kg, 1.5 mg/kg, 1.8 mg/kg, 2 mg/kg, 3 mg/kg, 4 mg/kg, or 5 mg/kg or any range of amounts created by using two of the aforementioned amounts as endpoints.

In some instances, the present disclosure provides a method of treating anhedonia in a subject in need thereof (e.g., human) comprising administering (e.g., orally) a therapeutically effective amount of Compound A to the subject, wherein the anhedonia includes the various types of anhedonia and disorders having symptoms of anhedonia described herein, including stress-induced depression, major depressive disorder (MDD), post-traumatic stress disorder (PTSD), schizophrenia, substance-related disorders, Parkinson's disease, sexual anhedonia, and social anhedonia, and wherein Compound A is administered at a dose of 0.5-10 mg/kg to the subject, such as 0.5-8 mg/kg, 1-10 mg/kg, or 1-8 mg/kg, including about 0.5 mg/kg, 0.8 mg/kg, 1 mg/kg, 1.5 mg/kg, 2 mg/kg, 2.5 mg/kg, 2.6 mg/kg, 2.8 mg/kg, 3 mg/kg, 3.5 mg/kg, 4 mg/kg, 4.5 mg/kg, 5 mg/kg, 5.2 mg/kg, 5.5 mg/kg, 6 mg/kg, 6.5 mg/kg, 7 mg/kg, 8 mg/kg, 9 mg/kg, or 10 mg/kg or any range of amounts created by using two of the aforementioned amounts as endpoints.

In some embodiments, the methods and uses described herein, such as the method of or use in treating anhedonia in a subject in need thereof (e.g., human), is achieved by administering (e.g., orally) a therapeutically effective amount of Compound A, such as 2 to 200 mg of Compound A in a single or multiple dosage units. For example, the method can include administering (e.g., orally), in a single or multiple dosage units, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 101 mg, about 102 mg, about 103 mg, about 104 mg, about 105 mg, about 106 mg, about 107 mg, about 108 mg, about 109 mg, about 110 mg, about 111 mg, about 112 mg, about 113 mg, about 114 mg, about 115 mg, about 116 mg, about 117 mg, about 118 mg, about 119 mg, about 120 mg, about 121 mg, about 122 mg, about 123 mg, about 124 mg, about 125 mg, about 126 mg, about 127 mg, about 129 mg, about 130 mg, about 131 mg, about 132 mg, about 133 mg, about 134 mg, about 135 mg, about 136 mg, about 137 mg, about 138 mg, about 139 mg, about 140 mg, about 141 mg, about 142 mg, about 143 mg, about 144 mg, about 145 mg, about 146 mg, about 147 mg, about 148 mg, about 149 mg, about 150 mg, about 151 mg, about 152 mg, about 153 mg, about 154 mg, about 155 mg, about 156 mg, about 157 mg, about 158 mg, about 159 mg, about 160 mg, about 161 mg, about 162 mg, about 163 mg, about 164 mg, about 165 mg, about 166 mg, about 167 mg, about 168 mg, about 169 mg, about 170 mg, about 171 mg, about 172 mg, about 173 mg, about 174 mg, about 175 mg, about 176 mg, about 177 mg, about 178 mg, about 179 mg, about 180 mg, about 181 mg, about 182 mg, about 183 mg, about 184 mg, about 185 mg, about 186 mg, about 187 mg, about 188 mg, about 189 mg, about 190 mg, about 191 mg, about 192 mg, about 193 mg, about 194 mg, about 195 mg, about 196 mg, about 197 mg, about 198 mg, about 199 mg, or about 200 mg or administering (e.g., orally) any range of amounts created by using two of the aforementioned amounts as endpoints. In some aspects, the method or use includes oral administration of 5 to 100 mg of Compound A in a single or multiple dosage units to a subject (e.g., a human). In some aspects, the method or use includes the oral administration of 5 to 80 mg of Compound A in a single or multiple dosage units to a subject (e.g., a human). In some aspects, the method or use includes oral administration of 5 to 40 mg of Compound A in a single or multiple dosage units to a subject (e.g., a human).

In some aspects, the methods and uses described herein, such as the method of or use in treating anhedonia in a subject in need thereof (e.g., human), is achieved by administering (e.g., orally) at least 5 mg of Compound A, such as at least 5, 10, 15, 20, 25, 30, 35, 50, 75, or 100 mg of Compound A. In some embodiments, the methods and uses described herein, such as the method of or use in treating anhedonia in a subject in need thereof, is achieved by administering (e.g., orally) at least 20 mg of Compound A per day, such as at least 30, 40, 60, 75, 85, 100, 125, 150, 175, or 200 mg of Compound A per day to a subject (e.g., a human). In some embodiments, the methods and uses described herein, such as the method of or use in treating anhedonia in a subject in need thereof, is achieved by administering (e.g., orally) at least 5 mg of Compound A one, two, three, four, or five days per week, such as at least 20, 40, 60, 75, 85, 100, 125, 150, 175, or 200 mg of Compound A is administered on one, two, three, four, or five days per week to a subject (e.g., a human). In some embodiments, Compound A is administered on every other day, every three days, or twice weekly.

In some embodiments, the methods and uses described herein, such as the method of or use in treating anhedonia in a subject in need thereof (e.g., a human), is achieved by administering (e.g., orally) a therapeutically effective amount of Compound A per day, such as 5 to 1000 mg of Compound A per day or per week, such as 5 to 500 mg or 5 to 250 mg of Compound A per day or per week. For example, the method or use can include administering (e.g., orally) about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, or about 1000 mg of Compound A per day, per week, or administering (e.g., orally) per day a range of amounts created by using two of the aforementioned amounts as endpoints. In some aspects, the method or use includes orally administering 5 to 200 mg of Compound A per day, such as 10, 15, 20, 25, 30, 35, or 40 mg to 75, 100, 125, 150, 175, or 200 mg of Compound A per day, including 5 to 150 mg per day to a subject (e.g., a human). In some aspects, the oral administration includes 10, 20, 30 40, 50, 75, 100, or 125 mg of Compound A per day, such as 100 mg per day to a subject (e.g., a human).

In certain instances, the above daily doses of Compound A are administered (e.g., orally) as multiple doses per day, such as in two, three, four, or five doses per day. For Example, a daily dose of 100 mg, maybe administered in five 20 mg, four 25 mg, three 33.3 mg, or two 50 mg doses throughout the day.

In some embodiments, the above daily doses of Compound A are administered (e.g., orally) as a single dose. For example, about 5, 10, 15, 20, 25, or 30 mg to about 50, 65, 75, 100, 125, or 150 mg of Compound A per day can be orally administered as a single dose, including 10-30 mg, 20-50 mg, and 30-80 mg per day as a single dose, such as 25-30 mg per day as a single dose. Relatedly, any of the doses of Compound A discussed in the preceding paragraphs may be included in a single unit dosage form or in multiple unit dosage forms, such as two, three, or four unit dosage forms.

In certain embodiments, the methods and uses described herein, when using the daily dosing disclosed herein, achieve a steady state for Compound A within 6 to 9 days, such as in about 1 week.

In some embodiments, the methods and uses described herein for treating anhedonia by administering (e.g., orally) Compound A include administering according to a 12-hour (i.e., twice-a-day), 24-hour (i.e., once-a-day), 48-hour (i.e., once-per-two-days), 72-hour, 96-hour, 5-day, 6-day, 1-week, or 2-week dosing regimen, particularly 12-hour, 24-hour, or 48-hour dosing regimens. Such regimens can involve administering any of the above-described doses or daily doses. For instance, the present disclosure provides methods of treating anhedonia in a subject in need thereof (e.g., a human), comprising administering (e.g., orally) a therapeutically effective amount of Compound A to the subject according to 12-hour, 24-hour, 48-hour, 72-hour, 96-hour, 5-day, 6-day, 1-week, or 2-week intervals, particularly 12-hour, 24-hour, or 48-hour intervals, wherein the amount of Compound A corresponds to any of the above-described doses or daily doses. In certain such embodiments, Compound A is orally administered to a human subject under fed conditions, e.g., from between about 30 minutes before to about 2 hour after eating a meal, including during a meal or within 15 minutes after eating a meal.

In additional embodiments, the above-discussed methods or uses of treating anhedonia by administering a therapeutically effective amount of Compound A comprises oral administration of Compound A to a human subject under fed conditions, e.g., from between about 30 minutes before to about 2 hour after eating a meal, including during a meal or within 15 minutes after eating a meal. In some embodiments, the oral administration of Compound A to a human subject under fed conditions significantly enhances the bioavailability and exposure of Compound A as compared to the oral administration of Compound A to the subject under fasted conditions. In some embodiments, the oral administration of Compound A to a human subject under fed conditions increases one or more pharmacokinetic parameters for Compound A (e.g., $C_{max}$, $AUC_{inf}$, $T_{max}$, $t\frac{1}{2}_{\lambda z}$, etc.) as compared to when the same amount of Compound A is orally administered to the subject under fasted conditions.

In certain embodiments, the methods and uses described herein administer Compound A in the form of a pharmaceutically acceptable oral composition that comprises Compound A and one or more pharmaceutically acceptable carriers or excipients. The amount of Compound A included in these compositions may correspond to one or more of the amounts described herein. In some embodiments, the compositions are a unit dose.

Examples of pharmaceutically acceptable oral compositions that comprise Compound A include solid formulations (such as tablets, capsules, lozenges, dragées, granules, powders, sprinkles, wafers, multi-particulates, and films), liquid formulations (such as aqueous solutions, elixirs, tonics, tinctures, slurries, suspensions, and dispersions), and aerosolized formulations (such as mists and sprays). In one embodiment, a pharmaceutically acceptable oral composition of Compound A includes a pediatric suspension or granulate. All above-noted amounts of Compound A may be included in such formulations, e.g., a capsule comprising 5, 10, 15, 10, 25, 30, or 35 mg of Compound A.

Examples of compositions suitable for parenteral administration of Compound A, include sterile injectable solutions, suspensions, or dispersions, including aqueous or oleaginous preparations, particularly aqueous. In some embodiments, Compound A is administered according to a method or use described herein in an injectable sterile aqueous formulation that includes a parenterally-acceptable diluent or solvent, such as water, Ringer's solution, isotonic sodium chloride solution, buffered aqueous solutions, and aqueous solutions containing a miscible alcohol, such as 1,3-butanediol. Additional suitable excipients for parenteral formulations of Compound A include, mono- or di-glycerides; fatty acids, such as oleic acid and its glyceride derivatives; natural pharmaceutically-acceptable oils, such as olive oil or castor oil, including their polyoxyethylated versions; long-chain alcohol diluents or dispersants, such as alkyl celluloses, including carboxymethyl cellulose; and surfactants, such as Tweens, Spans and other emulsifying agents or bioavailability enhancers.

In another embodiment, kits are provided for oral administration of Compound A for the treatment of anhedonia. Such kits comprise a plurality of oral unit dosage forms of Compound A in combination with instructions for orally administering Compound A.

Additional embodiments and examples of the present disclosure are described herein. These embodiments and examples are illustrative and should not be construed as limiting the scope of the claimed invention.

5. EXAMPLES

Studies were conducted to determine the effect of Compound A in rodent models of anhedonia, e.g., the Progressive Ratio Test (PRT). Additional studies are conducted to determine the effect, if any, of Compound A in accepted models of anhedonia.

5.1. Example 1

The Effect of Compound A on Motivation in Rats Trained to Respond for Food Available Under a Progressive Schedule of Reinforcement The objective of this study was to test the effect of Compound A (1, 3, or 8 mg/kg, p.o.) on motivation as measured by rats responding for food under a progressive ratio (PR) schedule of reinforcement. Test measures included the total number of lever presses, and number of rewards (food pellets) acquired (break point).

5.1.1. Introduction

The progressive ratio (PR) task is a cross species translational approach used as measure of motivational performance including as a measure of anhedonia (see, e.g., Hodos W., Science 1961, 134:943-944; Spierling et al., Physiol Behav. 2017, 177:99-106; Radke et al., Pharmacol Biochem Behav. 2015, 129:51-55; Hauser et al., Hormones and Behavior 2009, 56:364-375; Merali et al., Psychopharmacology 2003, 165:413-418; Marchese et al., Int J Neuropsychopharmacology 2013, 16:1611-1621; Karlsson et al., Hippocampus 2018, 28(7):512-522; Strauss et al., Schizophr Res. 2016, 170(1):198-204; and Gunthorpe et al., Epilepsia 2012, 53(3):412-424). In rodent species, the basic test design involves training subjects to lever press for a food reward (45 mg Bioserve pellets) under a schedule in which the number of responses required to achieve a pellet increased for successive reinforcers. The present study used a progression ratio derived from the equation ratio= $[5 \times e^{(0.2 \times reinforcer\ \#)} - 5]$, and was as follows: 2, 4, 6, 9, 12, 15, 20, 25, 32, 40, 50, 62, 77, 95, 118, 145, 178, etc. Rats were therefore required to lever press a progressively increasing number of times to gain each successive reward, until reaching a break point, i.e., not meeting the schedule requirement. The break point was determined when the rat failed to earn a pellet over a 20 minute period. This provided a quantitative measurement of effort the animal would expend for the given reinforcer, which was interpreted as a measure of motivation. Based on the amount of food acquired during a typical test session (e.g., a break point of 10-12, corresponds to 0.45-0.54 g food), responding is limited by the amount of effort the animal is willing to expend for a single food pellet, rather than factors such as satiety.

Rats may be categorized based on differences in PR breakpoint, i.e., "low" and "high" responders. Importantly "low" responders are not characterized by signs of ill health (e.g., reduced body weight), or sensorimotor deficit, but rather exhibit greater motivational anhedonia as measured by PRT. Motivational deficits are commonly seen in anhedonia associated with many neuropsychological disorders, such as depression, dementia, and schizophrenia (Lactôt et al., Alzheimer's and Dementia 2017, 13:84-100) and efficacy in treating "low" responder rats is indicative of efficacy in treating more significant or severe anhedonia.

The primary purpose of this proposal was to evaluate the effect of Compound A on motivational performance of Male Long Evans rats under a progressive ratio schedule. A large (N=32) cohort of rats were used and the effect of Compound A was investigated both in all rats, and also a "low" responder subgroup, based on the low tertile (N=11) cohort recorded over 5 days baseline responding prior to study commencement.

5.1.2. Study Schedule:

TABLE 1

| Key Study Events | |
|---|---|
| Study | Procedure |
| PR Training | PR Schedule Training |
| PR Task | Compound A - PR Schedule |

5.1.3. Experimental Materials
Investigational Drug(s)

5.1.3.1. Compound A (lot #12)

Dosage form: Compound A was suspended in 0.5% CMC-Na and 0.1% Tween 80 in purified water and sonicated until fully dissolved. Drug was administered at a volume of 10 mL/kg, orally.
Doses tested: 1, 3, 8 mg/kg.
Pretreatment time: 120 minutes.

5.1.3.2. D-Amphetamine (lot #11-MWC-62-1)

Dosage form: D-Amp was suspended in 0.9% saline and sonicated until fully dissolved. Drug was administered at a volume of 1 mL/kg, intraperitoneally.
Dose tested: 0.6 mg/kg.
Pretreatment time: 10 minutes.

5.1.4. Materials and Methods

Test System: Thirty-two (32) experimentally non-naïve male Long Evans rats were included in the study.

Selection and Allocation of Animals: All animals were deemed satisfactory for the study purpose with no overt signs of poor health.

Housing and Management of Test System: Animals were singly housed and maintained on a restricted diet regimen, in which they were fed approximately 18-20 g of standard laboratory chow once per day following the completion of study procedures (between 16:00 h and 18:00 h). Water was available ad-libitum, excluding during training/testing sessions. Animals were maintained on a 12 h/12 h light/dark cycle with all testing conducted during the animals' light cycle. All animal use procedures were performed in accordance with the principles of the Canadian Council on Animal Care (CCAC).

Progressive Ratio Schedule: Drug testing was conducted according to a repeated measures design with each animal receiving each treatment over repeated test sessions. 32 experimentally non-naïve male Long Evans rats served as test subjects.

Compound A was tested at 3 doses, plus vehicle control (0.5% CMC and 0.1% Tween 80 in purified water) and a reference control (D-amphetamine 0.6 mg/kg, i.p.) (i.e., 5 cycles), as outlined in Table 2, under the PR schedule. On intervening weekdays, all rats continued to be trained under standard conditions to maintain performance. Drug testing was conducted twice weekly with a 3-4 day washout period between treatment sessions. Consequently, drug testing took approximately 3 weeks to complete.

TABLE 2

| Treatment groups | |
|---|---|
| Group | Treatment |
| 1 | Vehicle; 0.5% CMC + 0.1% Tween 80 in purified water (p.o.) |
| 2 | Compound A (1 mg/kg, p.o.) |
| 3 | Compound A (3 mg/kg, p.o.) |
| 4 | Compound A (8 mg/kg, p.o.) |
| 5 | D-Amphetamine (0.6 mg/kg, i.p.) |

Statistical Analyses: The primary measures of performance from the PR schedule (i.e., # lever presses, # acquired rewards (break point), and session duration) were expressed as means and SEM. Data from each measure were analyzed by one-way repeated measures ANOVA (Statistica Version 11, Statsoft Inc. [2012]). Animals were also ranked based on their performance measured over 7 days prior to commencement of testing. Based on this ranking the animals were classified as either "low" responders (i.e., low tertile group, N=11) or "high" responders (i.e., high tertile group, N=11), and each performance measure was assessed by a two-way mixed factor ANOVA (treatment: within; subgroup: between) (Statistica Version 11, Statsoft Inc. [2012]). The middle tertile were excluded from the subgroup analysis. A log transformation was also conducted on the lever press data to reduce the skewed data distribution to normality. In the event of a significant main effect, planned post-hoc comparisons between vehicle and treatment groups were made (Dunnetts or LSD test). Significance was set at P<0.05.

5.1.5. Results

Figure 1:
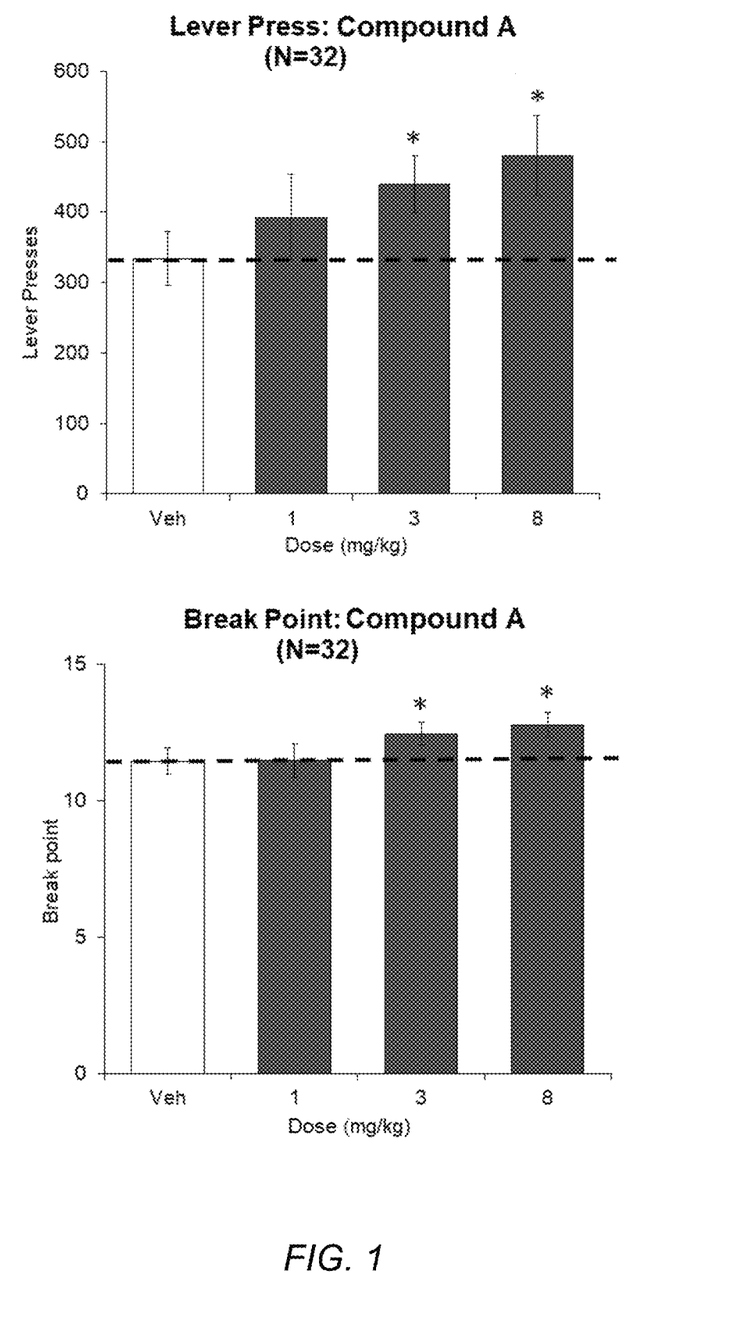
FIG. 1 shows the effects of Compound A (1, 3, and 8 mg/kg, p.o.) in the Progressive Ratio Test (PRT) for all rats (N=32). In both the lever press (upper graph) and break point (lower graph) measures, statistical significance ("asterisk") was observed at the 3 and 8 mg/kg doses ($p<0.05$ vs. Vehicle).

All rats (N=32): Analysis of vehicle and Compound A (1, 3, and 8 mg/kg) groups revealed a significant main effect on lever press ($F_{3,93}$=5.6; P<0.01) and break point ($F_{3,93}$=6.6; P<0.01). Subsequent Dunnett's test revealed a significant increase in both measures following Compound A (3 and 8 mg/kg) pretreatment relative to vehicle. For reference purpose, all rats received an additional pretreatment of D-amphetamine (0.6 mg/kg, i.p.). D-Amphetamine produced a significant increase in both lever press (Veh: 334+38; AMP: 893+131; P<0.01 paired T-test) and break point relative to vehicle pretreatment (Veh: 11.5+0.5; AMP: 14.7+0.7; P<0.01 paired T-test). See FIG. 1 and Tables 3-5.

TABLE 3

Lever Press Statistical Analysis (N = 32)

Repeated Measures Analysis of Variance with Effect Sizes and Powers
(Yellabelly)
Sigma-restricted parameterization
Effective hypothesis decomposition

| Effect | SS | DoF | MS | F | P | Partial eta-squared | Non-centrality | Observed power (alpha = 0.05) |
|---|---|---|---|---|---|---|---|---|
| Intercept | 21665476 | 1 | 21665476 | 86.15223 | 0.000000 | 0.735387 | 86.15223 | 1.000000 |
| Error | 7795848 | 31 | 251479 | | | | | |
| Treatment | 376841 | 3 | 125614 | 5.55929 | 0.001490 | 0.152062 | 16.67787 | 0.933908 |
| Error | 2101363 | 93 | 22595 | | | | | |

Dunnett's test; variable DV_1
(Yellabelly)
Probabilities for Post Hoc Tests (2-sided)
Error: Within MSE = 22595, DoF = 93.00

| Cell No. | Treatment | {1} 334.19 |
|---|---|---|
| 1 | Vehicle | — |
| 2 | Cmpd A (1 mg/kg) | 0.287039 |
| 3 | Cmpd A (3 mg/kg) | 0.017173 |
| 4 | Cmpd A (8 mg/kg) | 0.000599 |

TABLE 4

Break Point Statistical Analysis (N = 32)

Repeated Measures Analysis of Variance with Effect Sizes and Powers
(Yellabelly)
Sigma-restricted parameterization
Effective hypothesis decomposition

| Effect | SS | DoF | MS | F | P | Partial eta-squared | Non-centrality | Observed power (alpha = 0.05) |
|---|---|---|---|---|---|---|---|---|
| Intercept | 18600.38 | 1 | 18600.38 | 134.1940 | 0.000000 | 0.959487 | 734.1940 | 1.000000 |
| Error | 785.37 | 31 | 25.33 | | | | | |
| Treatment | 43.21 | 3 | 14.40 | 6.6301 | 0.000416 | 0.176191 | 19.8903 | 0.968508 |
| Error | 202.04 | 93 | 2.17 | | | | | |

TABLE 4-continued

Break Point Statistical Analysis (N = 32)

|  |  | Dunnett's test; variable DV_1 (Yellabelly) Probabilities for Post Hoc Tests (2-sided) |
|---|---|---|
| Cell |  | Error: Within MSE = 2.1725, DoF = 93.00 |
| No. | Treatment | {1} 11.469 |
| 1 | Vehicle | — |
| 2 | Cmpd A (1 mg/kg) | 0.999602 |
| 3 | Cmpd A (3 mg/kg) | 0.021630 |
| 4 | Cmpd A (8 mg/kg) | 0.001697 |

TABLE 5

Data (N = 32)

| | Vehicle | | | Cpmd A (1 mg/kg) | | | Cpmd A (3 mg/kg) | | |
|---|---|---|---|---|---|---|---|---|---|
| | Lever Press | Rewards | Sess. Duration | Lever Press | Rewards | Sess. Duration | Lever Press | Rewards | Sess. Duration |
| AVG | 334.2 | 11.5 | 17.1 | 392.4 | 11.5 | 16.9 | 439.3 | 12.5 | 22.6 |
| SEM | 38.0 | 0.5 | 1.0 | 60.9 | 0.6 | 1.6 | 40.2 | 0.4 | 2.0 |

| | Cpmd A (8 mg/kg) | | | D-Amphetamine (0.6 mg/kg) | | |
|---|---|---|---|---|---|---|
| | Lever Press | Rewards | Sess. Duration | Lever Press | Rewards | Sess. Duration |
| AVG | 479.8 | 12.8 | 21.1 | 893.0 | 14.7 | 44.8 |
| SEM | 56.7 | 0.5 | 1.4 | 130.5 | 0.7 | 3.1 |

Figure 2:
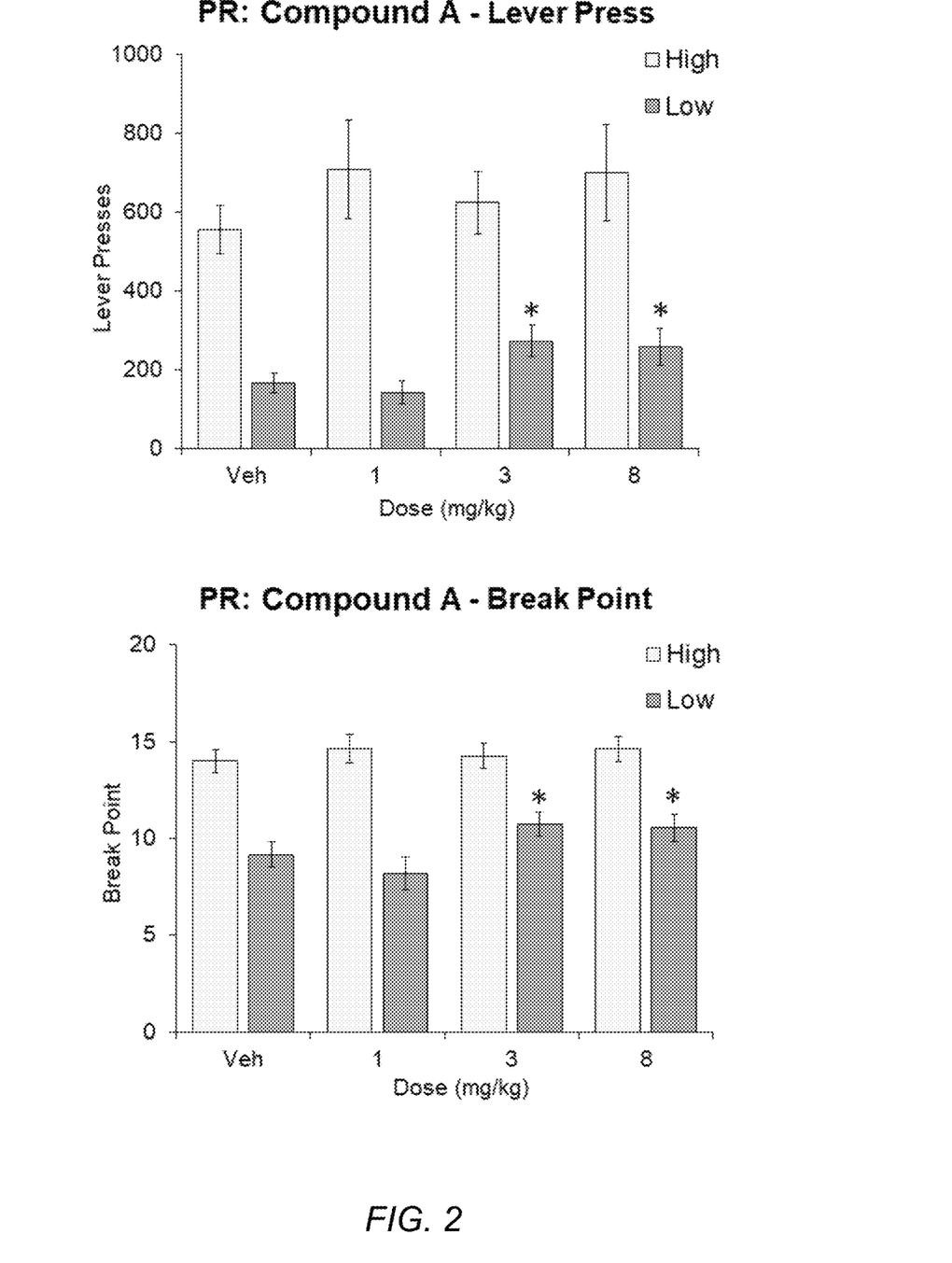
FIG. 2 shows the effects of Compound A (1, 3, and 8 mg/kg, p.o.) in the Progressive Ratio Test (PRT) for the rat "High" vs. "Low" responder subgroups (N=11/subgroup). In both the lever press (upper graph) and break point (lower graph) measures, statistical significance ("asterisk") was observed at the 3 and 8 mg/kg doses in the "Low" responder subgroups using two-way mixed factor ANOVA ($p<0.05$ vs. Vehicle).

"High" vs. "Low" responder subgroups (N=11/subgroup): On both measures of lever press and break point, two factor ANOVA revealed a main effect of subgroup (F1,20≥25.1; P<0.01), reflecting the overall difference in food maintained responding between the two extreme subgroups. On the measure lever press there was no main effect of treatment (F3,60=2.0; P=0.13; NS) or treatment x subgroup interaction (F3,60=1.7; P=0.17; NS), although following a log conversion a main effect of treatment (F3,60=4.2; P<0.01), and treatment x subgroup interaction (F3,60=4.7; P<0.01) was recorded. This reflected an effect of Compound A (3 and 8 mg/kg) pretreatment to selectively increase the number of lever presses in the "low" responder cohort. On the measure break point, a main effect of treatment (F3,60=3.3; P=0.03) and treatment x subgroup interaction (F3,60=3.6; P=0.02) further supported the effect of Compound A (3 and 8 mg/kg) to selectively increase responding for food in the "low" responder cohort. D-Amphetamine produced a significant increase in lever press and break point relative to vehicle pretreatment in both "low" and "high" responder subgroups (e.g., break point: "low" responders: Veh: 9.2±0.6; AMP: 12.2±1.2; P<0.01; "high" responders: 14.0±0.6; AMP: 17.5±0.9; P<0.01). See FIG. 2 and Tables 6-8.

TABLE 6

Lever Press Statistical Analysis (High v. Low Subgroupings)

Repeated Measures Analysis of Variance with Effect Sizes and Powers
(Yellabelly Split)
Sigma-restricted parameterization
Effective hypothesis decomposition

| Effect | SS | DoF | MS | F | P | Partial eta-squared | Non-centrality | Observed power (alpha = 0.05) |
|---|---|---|---|---|---|---|---|---|
| Intercept | 16141596 | 1 | 16141596 | 96.30559 | 0.000000 | 0.828039 | 96.30559 | 1.000000 |
| Intercept Split | 4208750 | 1 | 4208750 | 25.11066 | 0.000067 | 0.556646 | 25.11066 | 0.997434 |
| Error | 3352162 | 20 | 167608 | | | | | |
| Treatment | 164389 | 3 | 54796 | 1.95301 | 0.130714 | 0.088963 | 5.85904 | 0.479286 |
| Treatment Split | 144304 | 3 | 48101 | 1.71439 | 0.173626 | 0.078952 | 5.14318 | 0.426072 |
| Error | 1683439 | 60 | 28057 | | | | | |

TABLE 6-continued

Lever Press Statistical Analysis (High v. Low Subgroupings)

Log conversion:

Repeated Measures Analysis of Variance with Effect Sizes and Powers
(Yellabelly Split)
Sigma-restricted parameterization
Effective hypothesis decomposition

| Effect | SS | DoF | MS | F | P | Partial eta-squared | Non-centrality | Observed power (alpha = 0.05) |
|---|---|---|---|---|---|---|---|---|
| Intercept | 547.4941 | 1 | 547.4941 | 3276.203 | 0.000000 | 0.993932 | 3276.203 | 1.000000 |
| Intercept Split | 6.3442 | 1 | 6.3442 | 37.963 | 0.000005 | 0.654956 | 37.964 | 0.999949 |
| Error | 3.3422 | 20 | 0.1671 | | | | | |
| Treatment | 0.4484 | 3 | 0.1495 | 4.234 | 0.008828 | 0.174704 | 12.701 | 0.836773 |
| Treatment Split | 0.4943 | 3 | 0.1649 | 4.666 | 0.005370 | 0.189179 | 13.999 | 0.873834 |
| Error | 2.1185 | 60 | 0.0353 | | | | | |

LSD test; variable DV_1
(Yellabelly Split)
Probabilities for Post Hoc Tests
Error: Between; Within; Pooled MSE = 0.06826, DoF = 47.084

| Cell No. | Split | Treatment | {1} 2.7119 | {2} 2.7960 | {3} 2.7520 | {4} 2.7913 | {5} 2.1635 | {6} 2.0230 | {7} 2.3803 | {8} 2.3364 |
|---|---|---|---|---|---|---|---|---|---|---|
| 1 | High | Vehicle | | 0.298 | 0.618 | 0.326 | 0.000 | 0.000 | 0.005 | 0.002 |
| 2 | High | 1 mg/kg | 0.298 | | 0.585 | 0.953 | 0.000 | 0.000 | 0.001 | 0.000 |
| 3 | High | 3 mg/kg | 0.618 | 0.585 | | 0.620 | 0.000 | 0.000 | 0.002 | 0.001 |
| 4 | High | 8 mg/kg | 0.326 | 0.953 | 0.620 | | 0.000 | 0.000 | 0.001 | 0.000 |
| 5 | Low | Vehicle | 0.000 | 0.000 | 0.000 | 0.000 | | 0.085 | 0.009 | 0.035 |
| 6 | Low | 1 mg/kg | 0.000 | 0.000 | 0.000 | 0.000 | 0.085 | | 0.000 | 0.000 |
| 7 | Low | 3 mg/kg | 0.005 | 0.001 | 0.002 | 0.001 | 0.009 | 0.000 | | 0.586 |
| 8 | Low | 8 mg/kg | 0.002 | 0.000 | 0.001 | 0.000 | 0.035 | 0.000 | 0.586 | |

TABLE 7

Break Point Statistical Analysis (High v. Low Subgroupings)

Repeated Measures Analysis of Variance with Effect Sizes and Powers
(Yellabelly Split)
Sigma-restricted parameterization
Effective hypothesis decomposition

| Effect | SS | DoF | MS | F | P | Partial eta-squared | Non-centrality | Observed power (alpha = 0.05) |
|---|---|---|---|---|---|---|---|---|
| Intercept | 12720.05 | 1 | 12720.05 | 927.3935 | 0.000000 | 0.978889 | 927.3935 | 1.000000 |
| Intercept Split | 491.64 | 1 | 491.64 | 35.8442 | 0.000007 | 0.641861 | 35.8442 | 0.999901 |
| Error | 274.32 | 20 | 13.72 | | | | | |
| Treatment | 24.50 | 3 | 8.17 | 3.3302 | 0.142744 | 0.142744 | 9.9907 | 0.730034 |
| Treatment Split | 26.36 | 3 | 8.79 | 3.5836 | 0.018825 | 0.151952 | 10.7507 | 0.764364 |
| Error | 147.14 | 60 | 2.45 | | | | | |

LSD test; variable DV_1
(Yellabelly Split)
Probabilities for Post Hoc Tests
Error: Between; Within; Pooled MSE = 0.06826, DoF = 47.084

| Cell No. | Split | Treatment | {1} 2.7119 | {2} 2.7960 | {3} 2.7520 | {4} 2.7913 | {5} 2.1635 | {6} 2.0230 | {7} 2.3803 | {8} 2.3364 |
|---|---|---|---|---|---|---|---|---|---|---|
| 1 | High | Vehicle | | 0.344 | 0.684 | 0.344 | 0.000 | 0.000 | 0.002 | 0.001 |
| 2 | High | 1 mg/kg | 0.298 | | 0.588 | 1.000 | 0.000 | 0.000 | 0.000 | 0.000 |
| 3 | High | 3 mg/kg | 0.684 | 0.588 | | 0.586 | 0.000 | 0.000 | 0.001 | 0.000 |
| 4 | High | 8 mg/kg | 0.344 | 1.000 | 0.586 | | 0.000 | 0.000 | 0.000 | 0.000 |
| 5 | Low | Vehicle | 0.000 | 0.000 | 0.000 | 0.000 | | 0.139 | 0.024 | 0.046 |

TABLE 7-continued

| | | | | | | | | | | |
|---|---|---|---|---|---|---|---|---|---|---|
| Break Point Statistical Analysis (High v. Low Subgroupings) | | | | | | | | | | |
| 6 | Low | 1 mg/kg | 0.000 | 0.000 | 0.000 | 0.000 | 0.139 | | 0.000 | 0.001 |
| 7 | Low | 3 mg/kg | 0.002 | 0.000 | 0.001 | 0.000 | 0.024 | 0.000 | | 0.786 |
| 8 | Low | 8 mg/kg | 0.001 | 0.000 | 0.000 | 0.000 | 0.046 | 0.001 | 0.786 | |

TABLE 8

Figure 3:
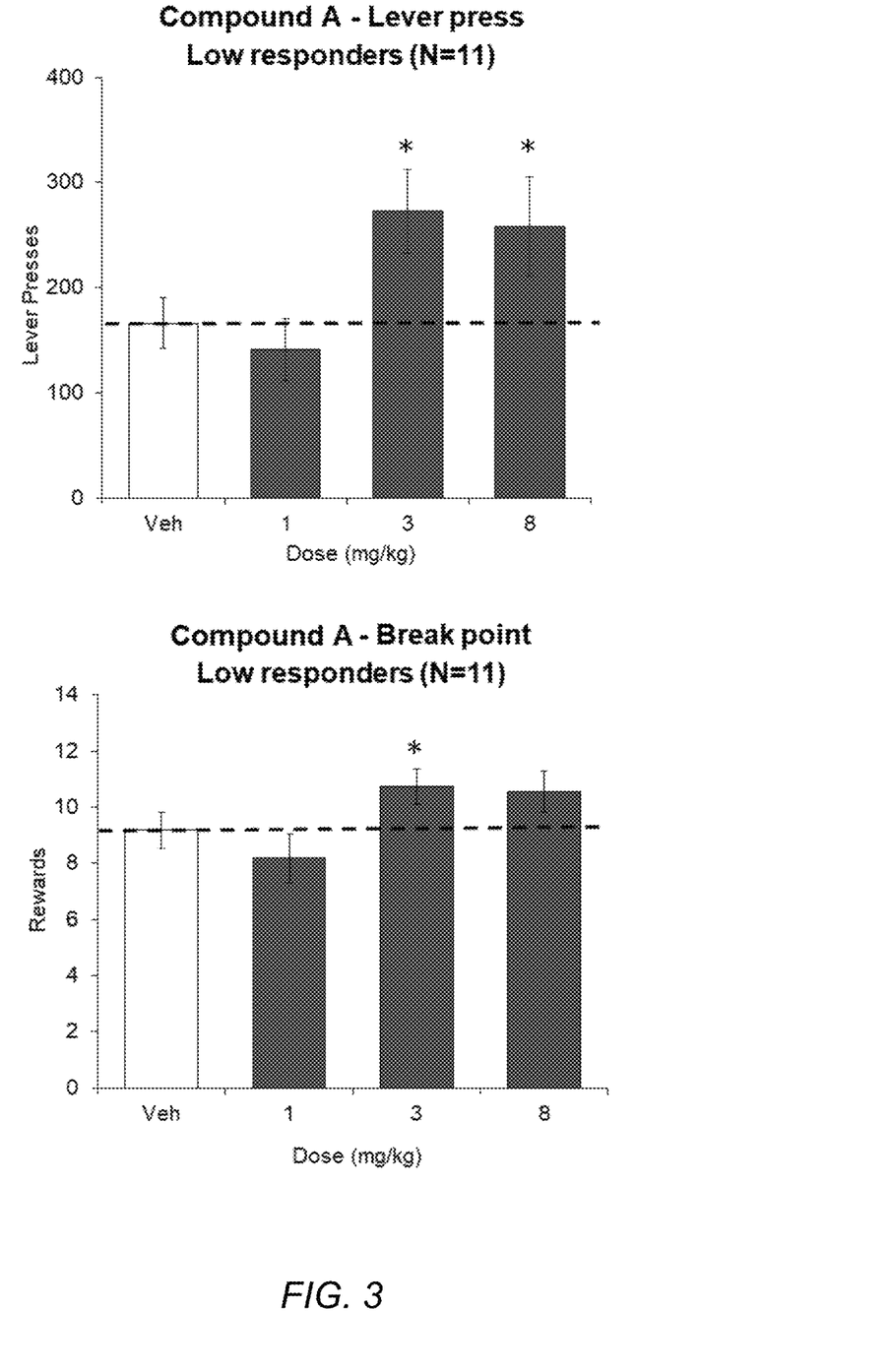
FIG. 3 shows the effects of Compound A (1, 3, and 8 mg/kg, p.o.) in the Progressive Ratio Test (PRT) for the rat "Low" responder subgroup (N=11/subgroup). In the lever press (upper graph) measure, statistical significance ("asterisk") was observed at the 3 and 8 mg/kg doses and in the break point (lower graph) measure, statistical significance ("asterisk") was observed at the 3 mg/kg doses using two-factor ANOVA of the low responder subgroup ($p<0.05$ vs. Vehicle).

Data (Low vs. High Subgroups) "Low" responder subgroup (N = 11): Restricting analysis to the "low" responder subgroup, identified a main effect of treatment on number of lever presses ($F3, 30 = 4.8$; $P < 0.01$) and break point ($F3, 30 = 5.6$; $P < 0.01$). See FIG. 3 and Table 9-10.

| | | Vehicle | | | Cpmd A (1 mg/kg) | | | Cpmd A (3 mg/kg) | | |
|---|---|---|---|---|---|---|---|---|---|---|
| Group | | Lever Press | Rewards | Sess. Duration | Lever Press | Rewards | Sess. Duration | Lever Press | Rewards | Sess. Duration |
| High | AVG | 556.5 | 14.0 | 17.5 | 707.5 | 14.6 | 21.2 | 623.9 | 14.3 | 24.3 |
| | SEM | 61.3 | 0.6 | 1.4 | 124.7 | 0.7 | 3.5 | 80.0 | 0.7 | 4.6 |
| Low | AVG | 166.2 | 9.2 | 15.8 | 141.5 | 8.2 | 15.5 | 272.7 | 10.7 | 23.2 |
| | SEM | 24.2 | 0.6 | 2.0 | 29.4 | 0.9 | 2.2 | 39.8 | 0.6 | 2.9 |

| | | Cpmd A (8 mg/kg) | | | D-Amphetamine (0.6 mg/kg) | | |
|---|---|---|---|---|---|---|---|
| Group | | Lever Press | Rewards | Sess. Duration | Lever Press | Rewards | Sess. Duration |
| High | AVG | 700.0 | 14.6 | 20.8 | 1406.6 | 17.5 | 52.4 |
| | SEM | 121.7 | 0.7 | 2.3 | 271.0 | 0.9 | 5.5 |
| Low | AVG | 258.0 | 10.5 | 22.6 | 462.7 | 12.2 | 44.5 |
| | SEM | 47.0 | 0.7 | 3.0 | 99.4 | 1.2 | 4.4 |

TABLE 9

Lever Press Statistical Analysis (Low Subgroup)

Repeated Measures Analysis of Variance with Effect Sizes and Powers
(Low Response Yellabelly)
Sigma-restricted parameterization
Effective hypothesis decomposition

| Effect | SS | DoF | MS | F | P | Partial eta-squared | Non-centrality | Observed power (alpha = 0.05) |
|---|---|---|---|---|---|---|---|---|
| Intercept | 19.32847 | 1 | 1932847 | 6853458 | 0.000009 | 0.872668 | 68.53458 | 1.000000 |
| Error | 282025 | 10 | 28203 | | | | | |
| Treatment | 141422 | 3 | 47141 | 4.78642 | 0.007661 | 0.323704 | 14.35925 | 0.858922 |
| Error | 295465 | 30 | 98.49 | | | | | |

| | | Dunnett's test; variable DV_1 (Low Response Yellabelly) Probabilities for Post Hoc Tests (2-sided) Error: Within MSE = 9848.8, DoF = 30.000 | |
|---|---|---|---|
| Cell | | | |
| No. | Treatment | {1} 166.18 | |
| 1 | Vehicle | — | |
| 2 | Cmpd A (1 mg/kg) | 0.887130 | |
| 3 | Cmpd A (3 mg/kg) | 0.045337 | |
| 4 | Cmpd A (8 mg/kg) | 0.095478 | |

TABLE 9-continued

Lever Press Statistical Analysis (Low Subgroup)

LSD test; variable DV_1
(Low Response Yellabelly)
Probabilities for Post Hoc Tests (2-sided)
Error: Within MSE = 9848.8, DoF = 30.000

| Cell No. | Treatment | {1} 166.18 | {2} 141.45 | {3} 272.73 | {4} 258.00 |
|---|---|---|---|---|---|
| 1 | Vehicle |  | 0.563361 | 0.017380 | 0.038072 |
| 2 | Cmpd A (1 mg/kg) | 0.563361 |  | 0.004162 | 0.009900 |
| 3 | Cmpd A (3 mg/kg) | 0.017380 | 0.004162 |  | 0.730251 |
| 4 | Cmpd A (8 mg/kg) | 0.038072 | 0.017380 | 0.730251 |  |

TABLE 10

Break Point Statistical Analysis (Low Subgroup)

Repeated Measures Analysis of Variance with Effect Sizes and Powers
(Low Repsonse Yellabelly)
Sigma-restricted parameterization
Effective hypothesis decomposition

| Effect | SS | DoF | MS | F | P | Partial eta-squared | Non-centrality | Observed power (alpha = 0.05) |
|---|---|---|---|---|---|---|---|---|
| Intercept | 4105.114 | 1 | 4105.114 | 282.8453 | 0.965852 | 0.965852 | 282.8453 | 1.000000 |
| Error | 145.136 | 10 | 14.514 |  |  |  |  |  |
| Treatment | 47.705 | 3 | 15.902 | 5.6093 | 0.003553 | 0.359356 | 16.8279 | 0.912118 |
| Error | 85.045 | 30 | 2.835 |  |  |  |  |  |

Dunnett's test; variable DV_1
(Low Response Yellabelly)
Probabilities for Post Hoc Tests (2-sided)
Error: Within MSE = 2.8348, DoF = 30.000

| Cell No. | Treatment | {1} 166.18 |
|---|---|---|
| 1 | Vehicle | — |
| 2 | Cmpd A (1 mg/kg) | 0.379636 |
| 3 | Cmpd A (3 mg/kg) | 0.098868 |
| 4 | Cmpd A (8 mg/kg) | 0.162039 |

LSD test; variable DV_1
(Low Response Yellabelly)
Probabilities for Post Hoc Tests (2-sided)
Error: Within MSE = 9848.8, DoF = 30.000

| Cell No. | Treatment | {1} 166.18 | {2} 141.45 | {3} 272.73 | {4} 258.00 |
|---|---|---|---|---|---|
| 1 | Vehicle |  | 0.173891 | 0.039512 | 0.067162 |
| 2 | Cmpd A (1 mg/kg) | 0.173891 |  | 0.001308 | 0.002550 |
| 3 | Cmpd A (3 mg/kg) | 0.039512 | 0.001308 |  | 0.801801 |
| 4 | Cmpd A (8 mg/kg) | 0.067162 | 0.002550 | 0.801801 |  |

5.1.6. Conclusions

The present study was designed to investigate the effects of Compound A (1, 3, and 8 mg/kg, p.o.) on motivation for food made available under a progressive ratio (PR) schedule of reinforcement. D-Amphetamine (0.6 mg/kg, i.p.) was included for reference purpose. A relatively large (N=32) cohort of rats were used for this study, and the effect of Compound A was investigated in all rats, and also in a "low" responder subgroup, based on responding measured over 5 days baseline prior to study commencement. The "low" responder subgroup model represents a behavioral phenotype of low motivation/anhedonia having more significantly lowered motivation/greater decisional anhedonia than the "high" responder group.

A robust effect of Compound A was found on both lever press and break point, with oral doses of 3 and 8 mg/kg significantly increasing both measures relative to vehicle pretreatment. Analysis of "high" and "low" responder subgroups identified the effect of Compound A as statistically significant in the "low" responder subgroup. The effect of Compound A differed from D-amphetamine in two respects: (1) magnitude of increase, (2) the effect of Compound A showed statistical significance only in "low" responders. This may suggest a more subtle effect of Compound A on CNS systems relevant to reward/motivation, relative to D-amphetamine.

All of the U.S. patents, U.S. patent application publications, U.S. patent applications, foreign patents, foreign patent applications, and non-patent publications referred to in this specification, including U.S. provisional appl. No. 63/147,742, filed Feb. 9, 2021, are incorporated herein by reference in their entireties.

Although the foregoing compositions, methods, and uses have been described in some detail to facilitate understanding, it will be apparent that certain changes and modifications may be practiced within the scope of the appended claims. Accordingly, the described embodiments are to be considered as illustrative and not restrictive, and the claimed invention is not to be limited to the details given herein, but may be modified within the scope and equivalents of the appended claims.

What is claimed is:

1. A method of treating anhedonia, comprising administering a therapeutically effective amount of Compound A to a human in need thereof;
   wherein Compound A is N-[4-(6-fluoro-3,4-dihydro-1H-isoquinolin-2-yl)-2,6-dimethylphenyl]-3,3-dimethylbutanamide.

2. A method of reversing hyperactivity in the ventral tegmental area (VTA, comprising administering an effective amount of Compound A to a human in need thereof;
   wherein Compound A is N-[4-(6-fluoro-3,4-dihydro-1H-isoquinolin-2-yl)-2,6-dimethylphenyl]-3,3-dimethylbutanamide; and
   wherein the human is suffering from anhedonia.

3. The method of claim 1 or 2, which comprises enhancing the opening of a Kv7 potassium channel in the human.

4. The method of claim 3, wherein the Kv7 potassium channel is one or more of Kv7.2, Kv7.3, Kv7.4, or Kv7.5.

5. The method of claim 4, which is selective for enhancing the opening of one or more of Kv7.2, Kv7.3, Kv7.4, or Kv7.5 over Kv7.1.

6. The method of claim 3, which comprises opening of the Kv7.2/Kv7.3 (KCNQ2/3) potassium channel.

7. The method of claim 1, wherein the anhedonia comprises sexual anhedonia.

8. The method of claim 1, wherein the anhedonia comprises social anhedonia.

9. The method of claim 1, wherein the anhedonia is a symptom of a neuropsychiatric disorder.

10. The method of claim 9, wherein the neuropsychiatric disorder is a depressive disorder, substance-related disorder, psychotic disorder, personality disorder, epileptic disorder, or a combination thereof.

11. The method of claim 10, wherein the neuropsychiatric disorder is a depressive disorder.

12. The method of claim 11, wherein the depressive disorder is stress-induced depression, major depressive disorder (MDD), post-traumatic stress disorder (PTSD), disruptive mood dysregulation disorder, persistent depressive disorder, bipolar spectrum disorder, bipolar depression, postpartum depression, premenstrual dysphoric disorder (PMDD), seasonal affective disorder (SAD), atypical depression, treatment-resistant depression (TRD), depression associated with agitation or anxiety, adjustment disorder with depressed mood, prolonged depressive reaction, or a combination thereof.

13. The method of claim 11, wherein the depressive disorder is MDD.

14. The method of claim 10, wherein the neuropsychiatric disorder is a substance-related disorder.

15. The method of claim 14, wherein the substance-related disorder comprises a dependency on alcohol, cocaine, opioids, or nicotine.

16. The method of claim 9, wherein the neuropsychiatric disorder is schizophrenia, extrapyramidal disorder, Alzheimer's disease, dementia, Parkinson's disease, schizoaffective disorder, schizotypal disorder, obsessive-compulsive disorder, PTSD, anorexia nervosa, panic disorder, attention deficit hyperactivity disorder (ADHD), or dysthymic disorder.

17. The method of claim 9, wherein the neuropsychiatric disorder is an epileptic disorder.

18. The method of claim 17, wherein the epileptic disorder is epilepsy, chronic headache including chronic migraine with or without aura, migraine aura without headache, chronic tension headache, hemicranias continua, new daily persistent headache, post stroke, dementia, multiple sclerosis, cancer, chronic pain, HIV/AIDs, lupus, or hypothyroidism.

19. The method of claim 1, wherein Compound A is administered at a dose of 2 to 200 mg to the human.

20. The method of claim 1, wherein Compound A is administered at a dose of 5 to 100 mg to the human.

21. The method of claim 1, wherein Compound A is administered at a dose of 5 to 80 mg to the human.

22. The method of claim 1, wherein Compound A is administered at a dose of 5 to 40 mg to the human.

23. The method of claim 1, wherein Compound A is administered at a dose of at least 5 mg to the human.

24. The method of claim 23, wherein Compound A is administered at a dose of at least 10 mg to the human.

25. The method of claim 23, wherein Compound A is administered at a dose of at least 20 mg to the human.

26. The method of claim 1, wherein Compound A is administered at a dose of 5-1000 mg per day or per week to the human.

27. The method of claim 26, wherein Compound A is administered at a dose of 5-500 mg per day or per week to the human.

28. The method of claim 26, wherein Compound A is administered at a dose of 5-250 mg per day or per week to the human.

29. The method of claim 26, wherein Compound A is administered at a dose of 5-150 mg per day to the human.

30. The method of claim 26, wherein Compound A is administered at a dose of 100 mg per day to the human.

31. The method of claim 1, wherein Compound A is administered at a dose of 0.05-20 mg/kg to the human.

32. The method of claim 31, wherein Compound A is administered at a dose of 0.1-5 mg/kg to the human.

33. The method of claim 1, wherein Compound A is orally administered to the human.

34. The method of claim 33, wherein Compound A is orally administered to the human from between about 30 minutes before to about 2 hours after eating a meal.

35. The method of claim 1, wherein the anhedonia, prior to treatment with Compound A, has a severity of at least 5 as measured by the Snaith-Hamilton Pleasure Scale (SHAPS).

36. The method of claim 35, wherein the anhedonia, prior to treatment with Compound A, has a severity of at least 9 as measured by SHAPS.

\* \* \* \* \*

UNITED STATES PATENT AND TRADEMARK OFFICE
CERTIFICATE OF CORRECTION

| | |
|---|---|
| PATENT NO. | : 11,957,675 B2 |
| APPLICATION NO. | : 17/668340 |
| DATED | : April 16, 2024 |
| INVENTOR(S) | : Simon Neil Pimstone |

It is certified that error appears in the above-identified patent and that said Letters Patent is hereby corrected as shown below:

In the Specification

At Column 1, immediately following the title, please add following section:
--RELATED APPLICATIONS
This application claims priority under 35 U.S.C. § 119(e) to U.S. provisional patent application, U.S.S.N. 63/147,742, filed on February 9, 2021, the entire contents of which is incorporated herein by reference.--

Signed and Sealed this
Tenth Day of September, 2024

Katherine Kelly Vidal
*Director of the United States Patent and Trademark Office*